(12) United States Patent
Park et al.

(10) Patent No.: US 11,197,918 B2
(45) Date of Patent: Dec. 14, 2021

(54) PHARMACEUTICAL COMPOSITION FOR PREVENTING OR TREATING NEOVASCULAR DISEASE, CONTAINING COLLAGEN TYPE I AND PIGMENT EPITHELIUM DERIVED FACTOR PEPTIDE AS ACTIVE INGREDIENTS

(71) Applicant: NexThera Co., Ltd., Gimhae-si (KR)

(72) Inventors: Sea Gwang Park, Busan (KR); Kug Hwan Roh, Busan (KR); Hyun Woong Kim, Busan (KR); Sung Jae Park, Busan (KR)

(73) Assignee: NexThera Co., Ltd., Gimhae-si (KR)

( * ) Notice: Subject to any disclaimer, the term of this patent is extended or adjusted under 35 U.S.C. 154(b) by 117 days.

(21) Appl. No.: 16/619,947

(22) PCT Filed: Jun. 8, 2018

(86) PCT No.: PCT/KR2018/006506
§ 371 (c)(1),
(2) Date: Dec. 6, 2019

(87) PCT Pub. No.: WO2018/226058
PCT Pub. Date: Dec. 13, 2018

(65) Prior Publication Data
US 2021/0077599 A1 Mar. 18, 2021

(30) Foreign Application Priority Data

Jun. 8, 2017 (KR) .................. 10-2017-0071521

(51) Int. Cl.
| | | |
|---|---|---|
| *A61K 38/39* | (2006.01) | |
| *A61K 9/00* | (2006.01) | |
| *A61K 9/06* | (2006.01) | |
| *A61K 9/08* | (2006.01) | |
| *A61K 38/57* | (2006.01) | |
| *A61P 27/02* | (2006.01) | |

(52) U.S. Cl.
CPC .............. *A61K 38/57* (2013.01); *A61K 38/39* (2013.01); *A61P 27/02* (2018.01)

(58) Field of Classification Search
None
See application file for complete search history.

(56) References Cited

FOREIGN PATENT DOCUMENTS

| KR | 10-2017-0123502 A | 11/2017 |
|---|---|---|
| WO | 2006/046584 A1 | 5/2006 |
| WO | 2016-014786 A2 | 1/2016 |

OTHER PUBLICATIONS

Emerson et al., "Emergent therapies for the treatment of neovascular age-related macular degeneration and diabetic macular edema," Biodrugs 21:245-257 (2007) (Year: 2007).*
Duh et al., "Vitreous levels of pigment epithelium derived factor in vascular endothelial growth factor: implications for ocular angiogenesis," Am J Ophthalmol 137:668-674 (2004) (Year: 2004).*
Diabetic retinopathy, Merck-accessed Jul. 3, 2021 at URL: merckmanuals.com/professional/eye-disorders/retinal-disorders/diabetic-retinopathy?query=ocular neovascular, 5 pages (Year: 2021).*
Nita et al., "Age-related macular degeneration and changes in the extracellular matrix," Med Sci Monit 20: 1003-1016 (2014) (Year: 2014).*
Immunization Grade Porcine Type I Collagen (Chondrex Inc., 2012, accessed Jul. 3, 2021 at URL web.archive.org/web/20121127104803/https://www.chondrex.com/products/immunization-grade-porcine-type-i-collagen). (Year: 2012).*
International Search Report for PCT/KR2018/006506 dated Feb. 18, 2019 from Korean Intellectual Property Office.
Hosomichi, Jun et al., "Involvement of the collagen I-binding motif in the anti-angiogenic activity of pigment epithelium-derived factor", Biochemical and Biophysical Research Communications, 2005, vol. 335, No. 3, pp. 756-761.
Filleur, Stephanie et al., "Two functional epitopes of pigment epithelial-derived factor block angiogenesis and induce differentiation in prostate cancer", Cancer Research, 2005, vol. 65, No. 12, pp. 5144-5152.
Belkacemi, Louiza et al., "Anti-tumor effects of pigment epithelium-derived factor (PEDF): implication for cancer therapy. A mini-review", Journal of Experimental & Clinical Cancer Research, 2016, vol. 35, inner pp. 1-14.
He, Xuemin et al., "PEDF and its roles in physiological and pathological conditions: implication in diabetic and hypoxia-induced angiogenic diseases", Clinical Science, 2015, vol. 128, No. 11, pp. 805-823.

* cited by examiner

*Primary Examiner* — Julie Ha
*Assistant Examiner* — Kristina M Hellman
(74) *Attorney, Agent, or Firm* — Revolution IP, PLLC (57) ABSTRACT

The present invention relates to a pharmaceutical composition for preventing or treating neovascular disease, including a collagen and a 34-mer pigment epithelium derived factor (PEDF) peptide as an active ingredient, more specifically, the combined administration of the collagen type I and the 34-mer pigment epithelium derived factor peptide increases the short antiangiogenic activity cycle of the PEDF and extends the dosage range of the PEDF to solve the discomfort and the side effects accordingly due to the conventional frequent injections and thus it can be applied as a therapeutic agent for various neovascular diseases.

6 Claims, 11 Drawing Sheets

Specification includes a Sequence Listing.

PHARMACEUTICAL COMPOSITION FOR PREVENTING OR TREATING NEOVASCULAR DISEASE, CONTAINING COLLAGEN TYPE I AND PIGMENT EPITHELIUM DERIVED FACTOR PEPTIDE AS ACTIVE INGREDIENTS

CROSS REFERENCE TO PRIOR APPLICATIONS

This application is a National Stage Application of PCT International Patent Application No. PCT/KR2018/006506 filed on Jun. 8, 2018, under 35 U.S.C. § 371, which claims priority to Korean Patent Application No. 10-2017-0071521 filed on Jun. 8, 2017, which are all hereby incorporated by reference in their entirety.

TECHNICAL FIELD

The present invention relates to a composition for preventing or treating neovascular disease comprising a collagen type I and a 34-mer pigment epithelium derived factor peptide as an active ingredient.

BACKGROUND ART

The macula is a neural tissue located in the center of the retina, which most of the visual cells are gathered in and the image of matter is formed on and is responsible for central visual acuity. Macular degeneration is an eye disease that progresses with age in many cases and causes degeneration of the macular area, causing vision disorders. In the early stages of this disease, vision is blurred, near vision is twisted, and later it leads to blindness.

Age-related macular degeneration is the most common cause of blindness in elderly people over 65 years old and the world's third largest blindness-causing disease, and 30 million people worldwide suffer from this disease, and about half a million patients are losing sight from the disease each year.

In Korea, 16.5% of people over 65 are suffering from early macular degeneration and the prevalence rate is gradually increasing due to the increase in elderly population. The time of onset is also getting younger from the sixties to the middle aged such as the forties or the fifties.

Age-related macular degeneration is classified into two types, atrophic and exudative types. Atrophic type occupies 90% of macular degeneration, and the central visual acuity loses gradually due to abnormalities such as retinal pigment epithelium in the macular area, and there is no treatment for restoring visual acuity loss other than no smoking, sun protection and taking antioxidants by mouth.

Exudative type also accounts for about 10% of the age-related macular degeneration, and has more rapid and severe impairment in visual acuity than the atrophic type. In case of exudative type, fundus abnormal findings such as choroidal neovascularization, retinal pigment epithelial detachment, sensory retinal detachment or retinal pigment epithelial rupture are accompanied. 70-90% of blindness due to age-related macular degeneration is known to be due to exudative lesions.

Pigment epithelium derived factor (PEDF) is a protein exhibiting antiangiogenic effects and is considered as a therapeutic agent for various diseases caused by angiogenesis. Currently, research is ongoing to use PEDF as a treatment for macular degeneration, but there is problems that a need for repeated injection due to short half-lives and a narrow range of concentrations applicable for the treatment of diseases. Accordingly, there is a need for a study that can maximize the effect of macular degeneration by solving the problems of the PEDF.

DISCLOSURE

Technical Problem

The present invention provides a composition comprising a collagen type I as an active ingredient to improve antiangiogenic effect of 34-mer pigment epithelium derived factor peptide, and an agent for preventing or treating ocular neovascular disease comprising a collagen type I and 34-mer pigment epithelium derived factor peptide, as an active ingredient.

Technical Solution

The present invention provides a composition for enhancing antiangiogenic effect of 34-mer pigment epithelium derived factor (PEDF) peptide comprising collagen type I as an active ingredient.

In addition, the present invention provides a pharmaceutical composition for preventing or treating ocular neovascular disease comprising a collagen type I and 34-mer pigment epithelium derived factor (PEDF) peptide composed with an amino acid represented by SEQ ID NO: 1, as an active ingredient, and wherein the collagen type I maintains the intraocular antiangiogenic effect of the PEDF peptide.

Advantageous Effects

According to the present invention, it is confirmed that when the 34-mer pigment epithelium derived factor peptide and the collagen type I are co-administered, the angiogenic effect by treatment with high dose of the 34-mer pigment epithelium derived factor peptide is suppressed and the antiangiogenic effect is maintained for a long time and thus the collagen type I can be utilized as a carrier or adjuvant of the 34-mer pigment epithelium derived factor peptide. In addition, when the collagen type I and the 34-mer pigment epithelium derived factor peptide are co-administered, the short antiangiogenic activity cycle of the 34-mer pigment epithelium derived factor peptide is increased to solve the discomfort and the side effects accordingly due to the conventional frequent injections and to extend the dosage range of the pigment epithelium derived factor, and thus it can be applied as a therapeutic agent for various neovascular diseases.

DESCRIPTION OF DRAWINGS

FIG. 1A and FIG. 1B show the results of confirming the degree of tube formation of each group after that HUVECs cells in which the tube formation was induced by the treatment with recombinant human VEGF-165 were treated with 0.2 mg/ml of avstin as a control and the 34-mer pigment epithelium derived factor peptides of 0.02, 0.2, 0.4, 1 and 5 pmol/ml, respectively and incubated for 4 hours. FIG. 1C and FIG. 1D show the results of confirming the degree of tube formation of each group after that HUVECs cells induced by VEGF- 165 were treated with collagen type I at concentrations of 0.01, 0.05, and 0.1%, and after 4 hours.

FIG. 2A and FIG. 2B are pictures taken with a microscope and a graph quantifying the size of neovascularization in which the control group was treated with PBS, and 0.01, 0.05, 0.1, and 10 pmol of the 34-mer pigment epithelium derived factor peptides were injected into the experimental group by intraocular injection for 5 days, respectively and photographed under the microscope 14 days after laser irradiation. FIG. 2C and FIG. 2D are pictures taken with a microscope and a graph quantifying the size of neovascularization in which the control group was treated with PBS, and 0.1, 0.5 and 1% of collagen type I were injected into the experimental group by intraocular injection, respectively and photographed under the microscope 14 days after laser irradiation.

FIG. 3A and FIG. 3B show a representative image result of the tube formation degree of each experimental group by fluorescence microscope, and a graph quantifying the degree of tube formation of each experimental group after that 0.05 and 0.1% of the collagen type I and 0.02, 0.2, 1, 10, 50, 100, 200, 500 and 1000 pmol/ml of the 34-mer pigment epithelium derived factor peptide were mixed, respectively and administered into a HUVECs cell model in which the tube formation was induced by treating with recombinant human VEGF-165.

FIG. 4A and FIG. 4B show a representative image result of the tube formation degree of each experimental group by fluorescence microscope, and a graph quantifying the degree of tube formation of each experimental group after that 0.1% of collagen type I, 0.1% of hyaluronic acid and 0.1% of gelatin were mixed with the 34-mer pigment epithelium derived factor peptides at concentrations of 0.02, 0.2, 1, 10, 50, 100, 200 and 500 pmol/ml, respectively and administered into a HUVECs cell model in which the tube formation was induced by treating with recombinant human VEGF-165.

FIG. 5A shows an experimental schedule of an animal model and a schematic diagram showing the timing of administration of 0.05 pmol of the 34-mer pigment epithelium derived factor peptide alone or 0.1% collagen type I alone or mixtures of 0.25, 2.5, 25, 50, 100 and 200 pmole of the 34-mer pigment epithelium derived factor peptides and 0.1% collagen type I, after laser irradiation. FIG. 5B and FIG. 5C show the result of confirming the size of the neovascularization area generated in each experimental group treated by the above method.

FIG. 6A and FIG. 6B shows a picture of anti-angiogenic effects and a graph quantifying the size of neovascularization of 0.1% of collagen type I alone treated group and 25 pmol of the 34-mer pigment epithelium derived factor peptide alone treated group and the mixture 0.1% of collagen type I and 25 pmol of the 34-mer pigment epithelium derived factor peptide treated group.

FIG. 2, FIG. 5 and FIG. 6 were experiments confirming the concept of the prophylactic effect by injection immediately after the irradiation, FIG. 7 is an experiment confirming the concept of the therapeutic effect. FIG. 7A shows an experimental schedule of an animal model and a schematic diagram showing the timing of treatment with 0.1% of collagen type I alone or 25 pmol of the 34-mer pigment epithelial factor peptide alone and the mixture of 0.1% of collagen type I and the 25 pmol 34-mer pigment epithelial factor peptide on day 7 after laser irradiation. FIG. 7B and FIG. 7C show the result of confirming the size of the neovascularization area generated in each experimental group treated by the above method.

FIG. 8A and FIG. 8B show the results of confirming the mechanism of action of each group of Western blotting of HUVECs cells which recombinant human VEGF-165 was treated followed by treatment with 0.2 or 1 pmol/ml of the 34-mer pigment epithelial factor peptide alone group, and the mixture group of 0.05% of the collagen type I and 1 pmol/ml of the 34-mer pigment epithelial factor peptide. The results confirmed the MAPK signaling mechanisms such as JNK, p38, and ERK and Akt signaling mechanisms included in the VEGF signaling mechanism, and Wnt/beta-catenin signaling mechanisms of the pigment epithelium derived factor signaling mechanism. FIG. 8C confirms whether tube formation is dependent on signaling by using inhibitors of the signaling mechanisms identified in FIG. 8A and FIG. 8B through tube formation experiments of HUVECs cells.

FIG. 10A is a schematic diagram illustrating the experimental process, FIG. 10B shows the result of confirming the decrease of the lesion size after the treatment with the mixture. FIG. 10C shows the reduction in lesion size after mixing the 34-mer pigment epithelium derived factor peptides at 5 and 25 pmole concentrations mixed with collagen or HA followed by treating it.

BEST MODE

The present invention may provide a composition for enhancing antiangiogenic effect of 34-mer pigment epithelium derived factor (PEDF) peptide comprising a collagen type I as an active ingredient.

The 34-mer pigment epithelium derived factor peptide may have concentration of 0.2 to 50 pmol/ml.

The collagen type I may be isolated from pigs.

The 34-mer pigment epithelium derived factor peptide may comprise an amino acid represented by SEQ ID NO: 1.

In addition, the present invention may provide a pharmaceutical composition for preventing or treating ocular neovascular disease comprising a collagen type I and 34-mer pigment epithelium derived factor (PEDF) peptide composed with an amino acid represented by SEQ ID NO: 1, as an active ingredient, and wherein the collagen type I maintains intraocular antiangiogenic effect of the PEDF peptide.

The 34-mer pigment epithelium derived factor peptide may have concentration of 0.2 to 50 pmol/ml and the collagen type I may be isolated from pigs.

The ocular neovascular disease may be selected from the group consisting of corneal neovascular disease, diabetic retinopathy and choroidal neovascular disease and age-related macular degeneration.

Figure 2:
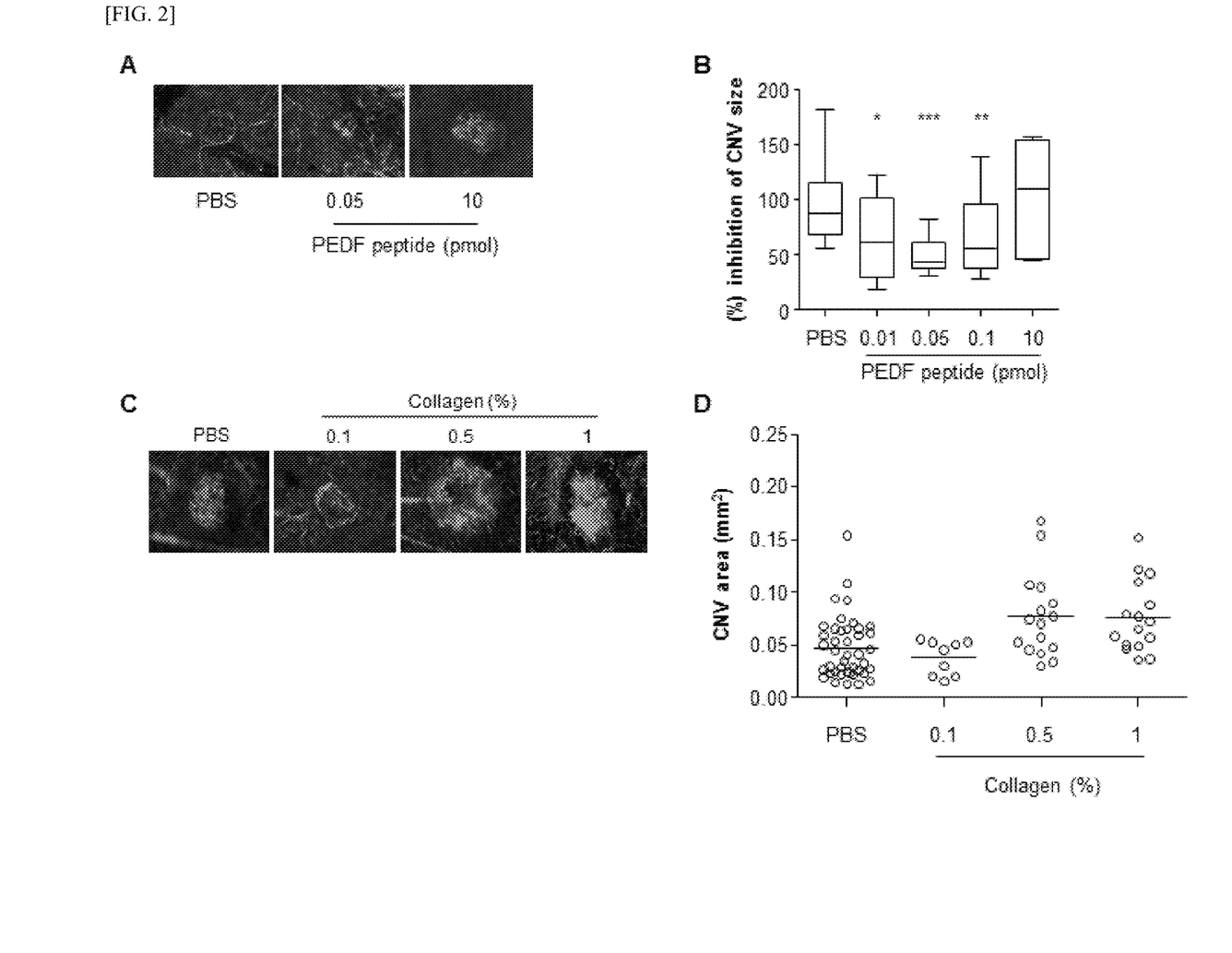
FIG. 2 shows the results of confirming the size of the lesion according to the administration concentration of the 34-mer pigment epithelium derived factor peptide and the collagen type I in mouse animal model inducing retinal lesions through laser irradiation.

According to one embodiment of the present invention, pigs-derived collagen type I at concentrations of 0.1, 0.5 and 1% was administered to experiment animals in which the retinal lesion was induced by irradiating laser and the Inhibitory effect of collagen on angiogenesis was confirmed and as shown in FIG. 2C and FIG. 2D, as the treatment concentration of collagen increases, angiogenesis is increased rather than suppressed.

From the above results, it was confirmed that a high concentration of collagen was unsuitable as a therapeutic agent for inhibiting angiogenesis.

Figure 3:
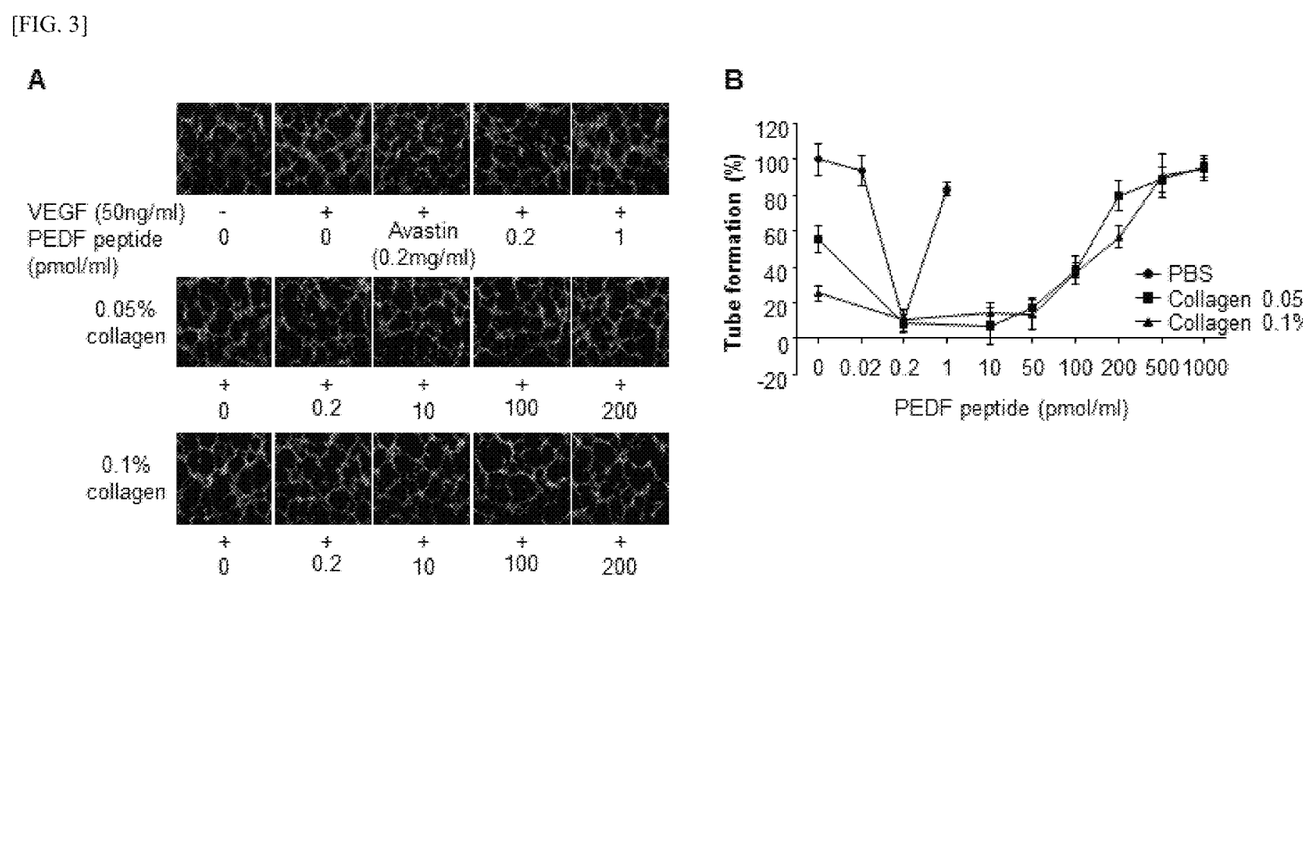
FIG. 3 shows the results of application availability of the collagen type I as a 34-mer pigment epithelium derived factor peptide carrier in the HUVECs cell model.

However, according to another embodiment of the present invention, a 34-mer pigment epithelium derived factor peptide was administered alone or in combination with collagen type I to HUVECs cells in which the tube formation was induced by treating with recombinant human VEGF-165 and as shown in FIG. 3, the inhibitory effect on tube formation in the 34-mer pigment epithelium derived factor peptide at 0.2 pmol/ml concentration alone administration group was similar to that of the 34-mer pigment epithelium derived factor peptide and collagen mixture administration group. In the experimental group administered with the 34-mer pigment epithelium derived factor peptide alone, the tube formation increased rapidly according to the increase of the concentration of the treated 34-mer pigment epithelium derived factor peptide, while in the experimental group administered with the mixture of the collagen type I and the 34-mer pigment epithelium derived factor peptide at high concentration, the tube forming inhibitory effect was continuously observed.

Figure 5:
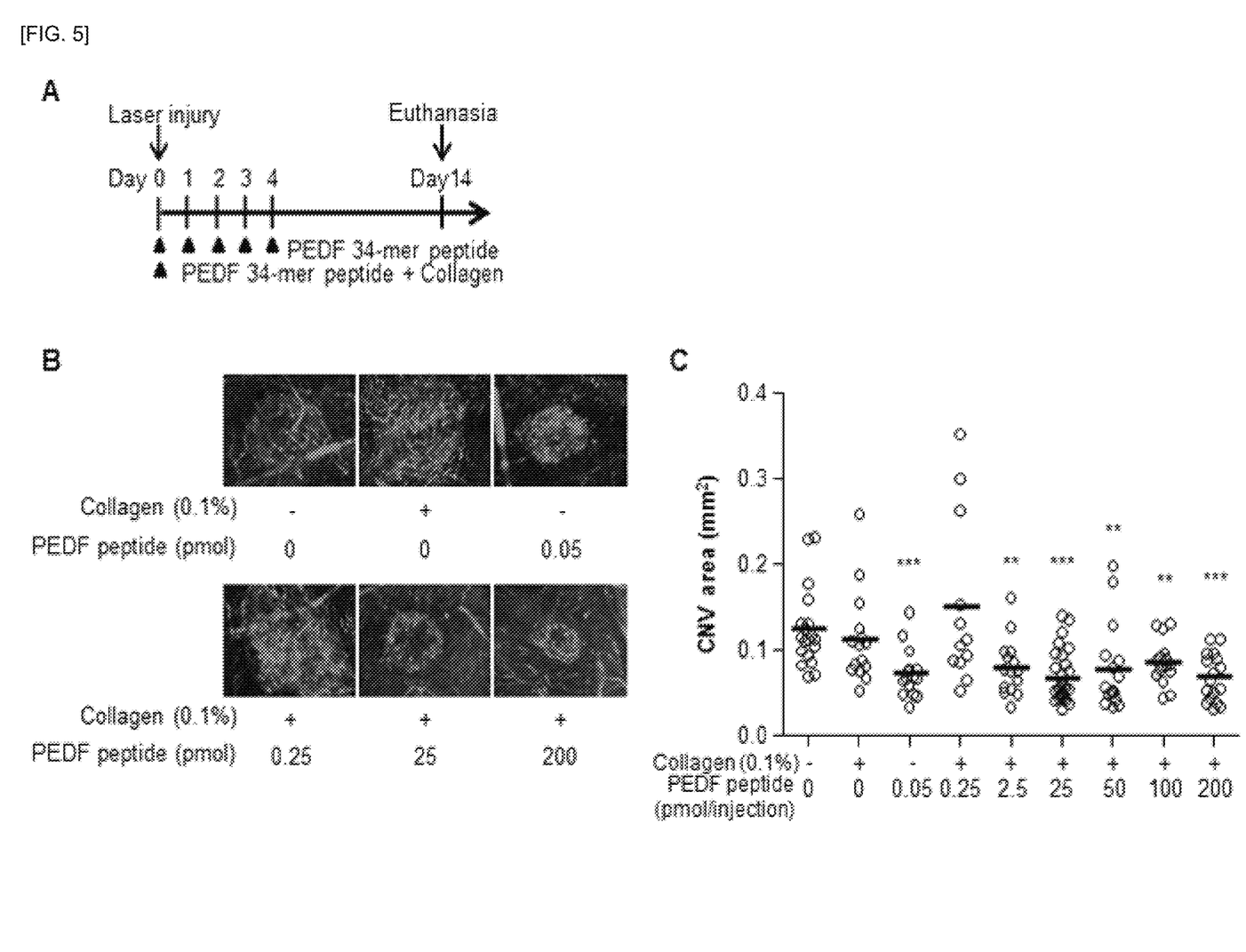
FIG. 5 shows the results of application availability of the collagen type I as a 34-mer pigment epithelium derived factor peptide carrier in an animal model in which the neovascularization was induced through laser irradiation.

In addition, a 34-mer pigment epithelium derived factor peptide alone or mixture of a pig-derived collagen type I at a concentration of 0.1% and a 34-mer pigment epithelium derived factor peptide was administered to experiment animals in which the retinal lesion was induced by irradiating laser and the Inhibitory effect of collagen on angiogenesis was confirmed and as shown in FIG. 5, the inhibitory effect on angiogenesis in the 34-mer pigment epithelium derived factor peptide alone administration group was similar to that of collagen of 0.1% and the 34-mer pigment epithelium derived factor peptide of 25 pmol mixture administration group. From the above results, it was confirmed that the effect of the administration of 5 times of the 34-mer pigment epithelium derived factor peptide at low concentration was similar to that of the administration of 1 time of the mixture of the 34-mer pigment epithelium derived factor peptide at high concentration and collagen type I.

Therefore, when a mixture of 34-mer pigment epithelial factor peptide and collagen type I is administered, the angiogenic effect of the pigment epithelial factor when treated at high doses is suppressed, and the number of administrations of the pigment epithelial factor is reduced and antiangiogenic effect can be maintained for a long time.

The pharmaceutical composition may comprise 0.01 to 50 weight % of a 34-mer pigment epithelium derived factor and 50 to 99.99 weight % of collagen type I.

The pharmaceutical composition may be provided as a form of eye drops; a gel ophthalmic ointment or injection comprising the collagen type I and the 34-mer pigment epithelium derived factor peptide composed with an amino acid represented by SEQ ID NO: 1 in combination with a pharmaceutically acceptable carrier.

In another embodiment of the present invention, a pharmaceutical composition for preventing or treating neovascular disease comprising the collagen type I and the 34-mer pigment epithelium derived factor peptide composed with an amino acid represented by SEQ ID NO: 1 may further comprise at least one additives selected from the group consisting of carriers, excipients, disintegrants, sweeteners, coatings, swelling agents, slip modifiers, flavoring agents, antioxidants, buffers, bacteriostatic agents, diluents, dispersants, surfactants, binders and lubricants, which are suitably and commonly used in the manufacture of pharmaceutical compositions.

Examples of the carrier, excipient and diluent include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil. Solid formulations for oral administration include tablets, pills, powders, granules, capsules, etc., and such solid formulations may contain at least one excipient such as starch, calcium carbonate, sucrose or lactose, gelatin and the like in addition to the composition. Furthermore, in addition to simple excipients, lubricants such as magnesium stearate and talc are also used. Examples of the liquid formulations for oral administration include suspensions, solutions, emulsions, syrups and the like, and various excipients such as wetting agents, sweeteners, fragrances, preservatives and the like may be included in addition to water and liquid paraffin which are commonly used as simple diluents. Formulations for parenteral administration include sterile aqueous solutions, non-aqueous solutions, suspensions, emulsions, freeze-dried preparations, and suppositories. Examples of the non-aqueous solution and the suspension include propylene glycol, polyethylene glycol, vegetable oil such as olive oil, injectable ester such as ethyl oleate, and the like. As the base of the suppository, witepsol, macrogol, tween 61, cacao butter, laurinum, glycerogelatin and the like can be used.

According to one embodiment of the present invention, the pharmaceutical composition may be administered intravenously, intraarterially, intraperitoneally, intramuscularly, intraperitoneally, intrasternally, transdermally, nasally, inhaled, topically, rectally, orally, intraocularly or intradermally to the subject in a conventional manner.

Preferred dosages of the peptides can vary depending on the condition and weight of the subject, the type and degree of the disease, the form of the drug, the administration route and duration and can be appropriately selected by those skilled in the art.

In the present invention, the 'subject' may be a mammal including a human, but it is not limited thereto.

Hereinafter, the present invention will be described in detail with reference to the following examples. The examples are only for describing the present invention in more detail and it is obvious to those skilled in the art that that the scope of the present invention is not limited by these examples embodiments in accordance with the gist of the present invention.

<Experimental Example 1> Tube Formation Assay 48-well plates were coated with 200 µl Matrigel and maintained at 37° C. for 1 hour, and HUVECs cells were stained with Calcein-AM for 15 minutes at 37° C.

The stained HUVECs cells were dispensed into $2 \times 10^4$ cells in each well of a Matrigel-coated plate and treated with recombinant human VEGF-165 into each well to induce the tube formation of the cells.

Thereafter, collagen type I (collagen type I alpha 1, partial [*Sus scrofa*] GenBank: AAR03833.1) and 34-mer pigment epithelium derived factor peptide (DPFFK VPVNK LAAAV SNFGY DLYRV RSSTS PTTN: SEQ ID NO: 1) were treated separately, respectively, or mixed together and treated and incubated for 4 hours at 37° C., and the degree of tube formation of each group was confirmed.

The degree of tube formation was confirmed by taking pictures with a Micromanipulator (Olympus) and compared by measuring the length of the tube.

<Experimental Example 2> Fabrication of Choroidal Neovascularization Model 5-8 week old C57BL/6 mice were purchased from Orient and used.

The pupils of each mouse were dilated using 5 mg/mL Tropicamide (santen pharmaceutical co. ltd, Kita-ku, Osaka, Japan) eye drops and 100 mg/kg ketamine (Huons, SEONG-NAM-SI, GYEONGGI-DO, Korea) and 10 mg/kg xylazine (BAYER, Leverkusen, Germany) were anesthetized by intraperitoneal injection.

After anesthesia, the mice were fixed to the mouse holder, and a laser beam of 150 to 210 mW intensity was irradiated for 0.1 second using a slit lamp microscope laser system to prepare four lesions of 50-100 µm size in the retinas of mice at 3, 6, 9 and 12 o'clock. At this time, droplets should be formed by the laser beam, which are important for breaking Bruch's membranes to form neovascularization (CNV).

Immediately after the production of lesions in the retina, PBS was injected into the vitreous body of the mouse eye in the control group, and collagen type I, 34-mer pigment epithelium derived factor peptide and a mixture of collagen type I and 34-mer pigment epithelium derived factor peptide were injected into the vitreous body of the mouse eye in the experimental group and the administration was performed in the same manner once a day for 1 day or 5 days.

On day 14 after laser irradiation, mice in each experimental group were anesthetized using ketamine (100 mg/kg) and xylazine (10 mg/kg), and 25 mg/ml FITC-dextran (Sigma Aldrich, St. Louis, Mo., USA) of 100 µl was injected retro-orbital to stain retinal vessels for 30 minutes.

The stained eyeball was separated and placed in 10% formalin to fix for 30 minutes, and then muscles, corneas, irises, lenses and vitreous bodies around the eyeball were carefully removed not to hurt the eye's retina fixed on the microscope and four sections were cut at 3, 6, 9, and 12 o'clock, covered with coverslip, the lesion was photographed using a fluorescence microscope, and the size was measured to compare with the control group.

<Example 1> Identification of Limits of 34-Mer Pigment Epithelium Derived Factor Peptides The antiangiogenic effects of the 34-mer pigment epithelium derived factor peptide (SEQ ID NO: 1) were confirmed in the tube formation assay of Experimental Example 1 and the choroidal neovascularization model of Experimental Example 2.

Figure 1:
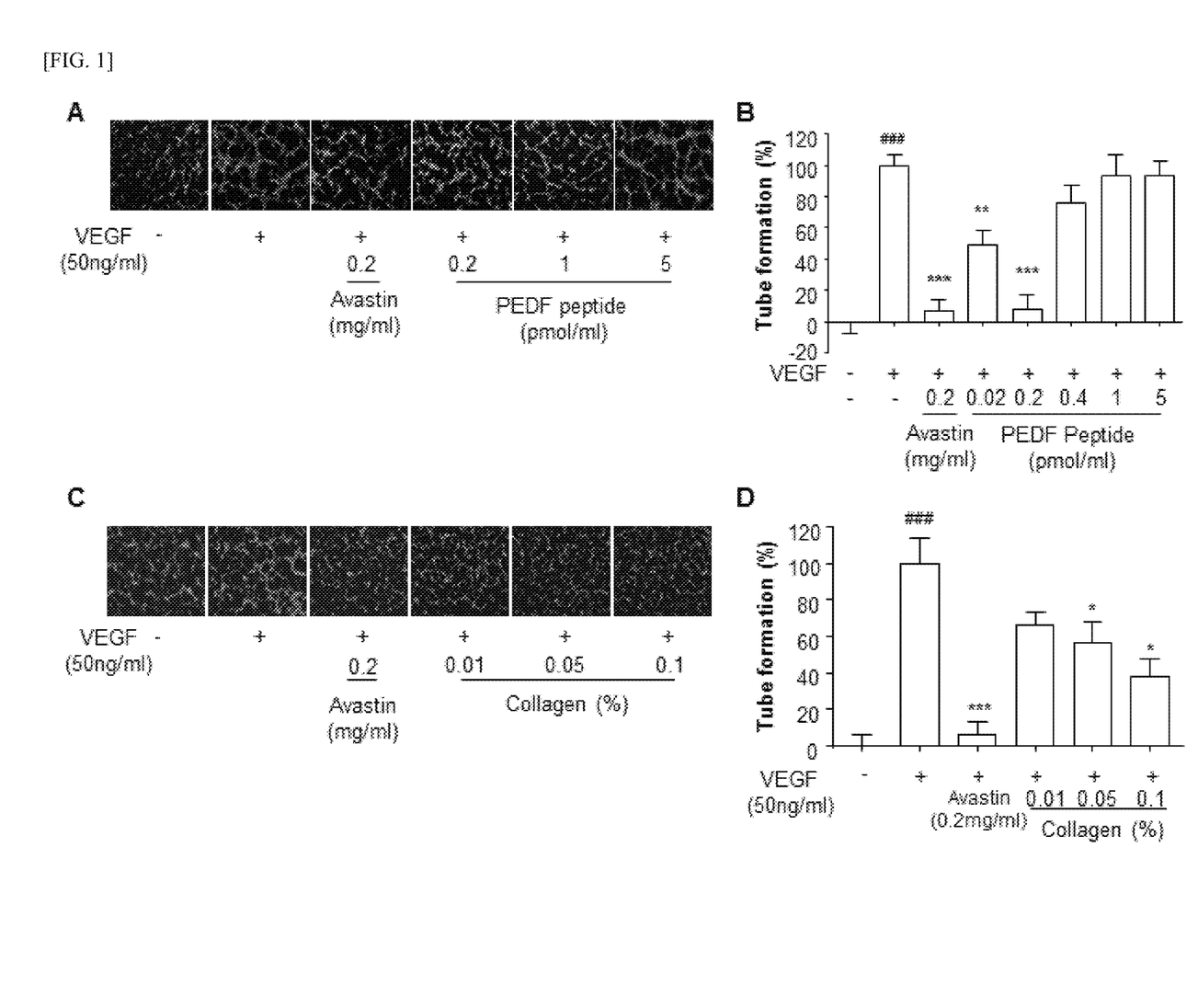
FIG. 1 shows the effect of inhibiting tube formation according to the administration concentration of 34-mer pigment epithelium derived factor (PEDF) peptide and collagen type I isolated from pigs in HUVECs cell model.

As a result, as shown in FIG. 1A and FIG. 1B, the experimental group treated with 0.2 pg/ml 34-mer pigment epithelium derived factor peptide exhibited the greatest inhibitory effect on tube formation, but at higher concentrations, the tube formation increased again. In addition, as shown in the laser-induced neovascularization (CNV) model of FIG. 2A and FIG. 2B, the treatment with the 34-mer pigment epithelium derived factor peptide of 0.01, 0.5 and 0.1 pmol was significantly reduced, but the treatment with a high concentration of 10 pmol was confirmed to increase neovascularization (CNV) again.

From the above results, the 34-mer pigment epithelium derived factor peptide showed the effect of inhibiting tube formation and laser-induced neovascularization, but when the treatment of 34-mer pigment epithelium derived factor peptide at high concentration was confirmed to induce neovascularization again and thus it was confirmed that the concentration of the 34-mer pigment epithelium derived factor peptide to be treated for neovascularization inhibition is very limited.

<Example 2> Confirmation of Antiangiogenic Effect of Collagen Type I

To confirm the effect of collagen type I on tube formation and angiogenesis, HUVECs cells prepared as in Experimental Example 1 were treated with collagen type I extracted from pig collagen at 0.01, 0.05 and 0.1% concentrations, respectively and the degree of tube formation was confirmed.

As a result, as shown in FIG. 1O and FIG. 1D, the tube formation by collagen was suppressed in a concentration-dependent manner.

However, as a result of administering collagen type I isolated from pigs at 0.1, 0.5 and 1% concentration to the experimental animals in which the retinal lesions were induced and confirming the angiogenesis inhibitory effect of the collagen, as the collagen treatment concentration increased as shown in FIG. 2C and FIG. 2D, angiogenesis size was increased.

From the above results, it was confirmed that a high concentration of collagen was unsuitable as a therapeutic agent for inhibiting angiogenesis.

<Example 3> Confirmation of Effect of Combined Treatment of Collagen Type I and 34-Mer Pigment Epithelium Derived Factor Peptide in Tube Formation Model The possibility of collagen type I as a 34-mer pigment epithelium derived factor peptide carrier was confirmed by using the tube formation model.

As a result of administering the 34-mer pigment epithelium derived factor peptide alone or its mixture with collagen type I to the tube formation model prepared as in Experimental Example 1, as shown in FIG. 3, the inhibitory effect on tube formation in the 34-mer pigment epithelium derived factor peptide at 0.2 pmol/ml concentration alone administration group was similar to that of the 34-mer pigment epithelium derived factor peptide and collagen mixture administration group. However, in the experimental group administered with the 34-mer pigment epithelium derived factor peptide at high concentration alone, the tube formation increased rapidly, while in the experimental group administered with the mixture of the collagen type I and the 34-mer pigment epithelium derived factor peptide at high concentration, the tube forming inhibitory effect was continuously observed.

From the above results, co-administration with collagen type I may be proposed as a method for solving the problem of the narrow treatment concentration range of 34-mer pigment epithelium derived factor peptide.

<Example 4> Confirmation of Effect of Combined Treatment of Collagen Type I or Other Drug Carrier with 34-Mer Pigment Epithelium Derived Factor Peptide in Tube Formation Model In order to identify the most suitable carrier of the 34-mer pigment epithelium derived factor peptide through tube formation model, it was combined treated with various materials.

34-mer pigment epithelium derived factor peptide was administered alone or it was mixed with collagen type I, hyaluronic acid and gelatin, respectively, and administered, to the tube formation model of HUVECs cells and the effect of inhibiting the tube formation was confirmed.

Figure 4:
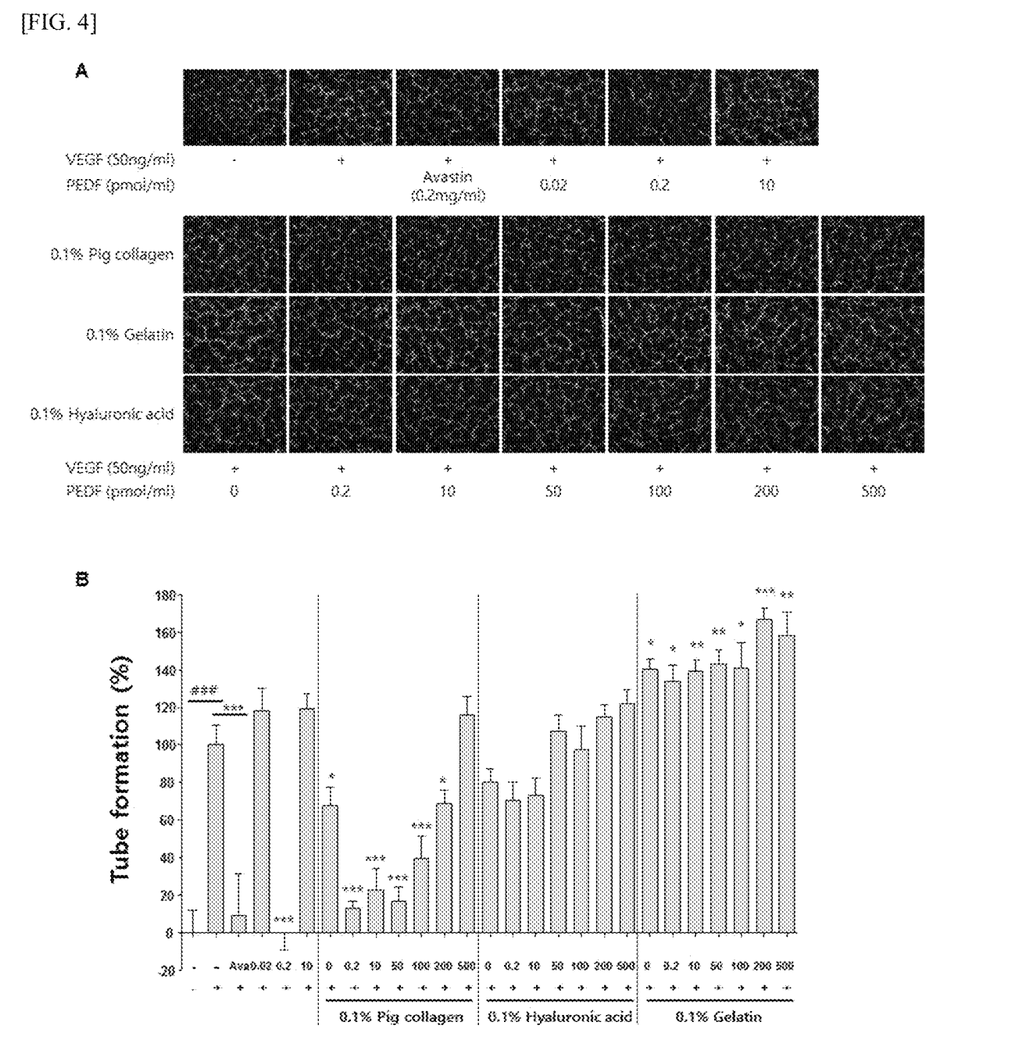
FIG. 4 shows a result of confirming the inhibitory effect on tube formation after that to identify suitable carriers of the 34-mer pigment epithelium derived factor peptide in a HUVECs cell model, the cells were treated with hyaluronic acid (HA), gelatin and collagen type I alone or in combination with the 34-mer pigment epithelium derived factor peptide.

As a result, as shown in FIG. 4, the inhibitory effect in the 34-mer pigment epithelium derived factor peptide alone administration group was same as that of the 34-mer pigment epithelium derived factor peptide and collagen type I mixture administration group, while no significant inhibitory effect on tube formation was found in the model group treated with mixture with hyaluronic acid. In addition, it was confirmed that the tube formation was increased only by gelatin alone, and when the gelatin and 34-mer pigment epithelium derived factor peptide were administered in combination, rather, the tube formation was confirmed to increase.

From the above results, it was confirmed that collagen type I was most suitable as a substance capable of expanding the therapeutically effective concentration range of the 34-mer pigment epithelium derived factor peptide.

<Example 5> Confirmation of Effect of Combined Treatment of Collagen Type I and 34-Mer Pigment Epithelium Derived Factor Peptide in Choroidal Neovascularization Animal Model The possibility of collagen type I as a 34-mer pigment epithelium derived factor peptide carrier identified in previous experiments was confirmed in choroidal neovascularization animal models.

First, the choroidal neovascularization animal model prepared as in Experimental Example 2 was injected 5 times with 34-mer pigment epithelium derived factor peptide of 0.05 pmol concentration and 0.1% collagen type I and 34-mer pigment epithelium derived factor peptides at 0.25, 2.5, 25, 50, 100 and 200 pmol concentrations were injected once into the 34-mer pigment epithelium derived factor peptide and the collagen type I mixture administration group in the same manner as in FIG. 5A.

As a result, as shown in FIG. 5B and FIG. 5C, the angiogenesis inhibitory effect of 34-mer pigment epithelium derived factor peptide at high concentration and collagen type I mixture administration group was similar to that of 34-mer pigment epithelium derived factor peptide at low concentration alone administration group.

From the above results, it is confirmed that when the 34-mer pigment epithelium derived factor peptide and the collagen type I are co-administered, the angiogenic effect by treatment with high dose of the 34-mer pigment epithelium derived factor peptide is suppressed and the frequency of administration of the 34-mer pigment epithelium derived factor peptide can be reduced and the antiangiogenic effect thereof can be maintained for a long time.

Meanwhile, to confirm whether the combined treatment effect of the collagen type I and the 34-mer pigment epithelium derived factor peptide is due to the presence of the collagen type I, the prepared choroidal neovascularization animal models were divided into groups of PBS alone administration control group, 0.1% collagen type I alone administration group, 25 pmol of 34-mer pigment epithelium derived factor peptide alone administration group and 0.1% collagen type I and 25 pmol 34-mer pigment epithelium derived factor peptide mixture administration group, and they were each administered once immediately after laser irradiation.

Figure 6:
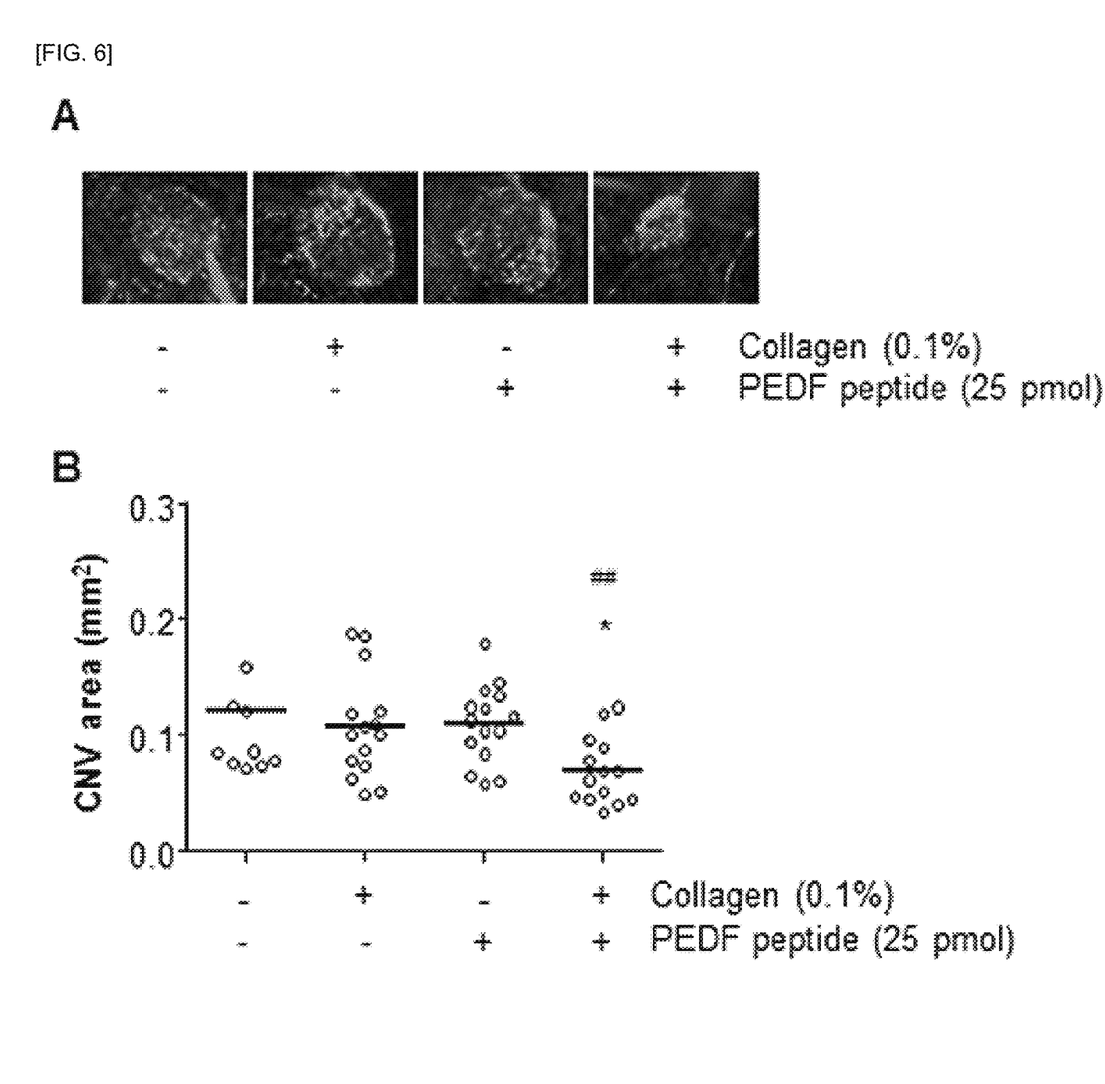
FIG. 6 shows the results of confirming whether the antiangiogenic effect of mixture of the 34-mer pigment epithelium derived factor peptide and the collagen type I in the animal model in which the neovascularization was induced through laser irradiation is due to the presence of collagen type I.

As a result, as shown in FIG. 6A and FIG. 6B, the angiogenesis inhibitory effect of each alone treatment group was similar to that of the control group, but the angiogenesis inhibitory effect was confirmed in the mixture treatment group.

From these results, it was confirmed that collagen type I plays an important role in maintaining the antiangiogenic effect of the 34-mer pigment epithelium derived factor peptide while reducing the frequency of drug administration. Therefore, it was confirmed that collagen type I can be utilized as a drug carrier or adjuvant of the 34-mer pigment epithelium derived factor peptide, and the combined administration of the collagen type I and the 34-mer pigment epithelium derived factor peptide prolongs the short antiangiogenic activity cycle of the 34-mer pigment epithelium derived factor peptides to solve the discomfort and the side effects accordingly due to the conventional frequent injections of the 34-mer pigment epithelium derived factor peptides and to extend the dosage range of the 34-mer pigment epithelium derived factor, and thus it can be applied as a therapeutic agent for various neovascular diseases.

Figure 7:
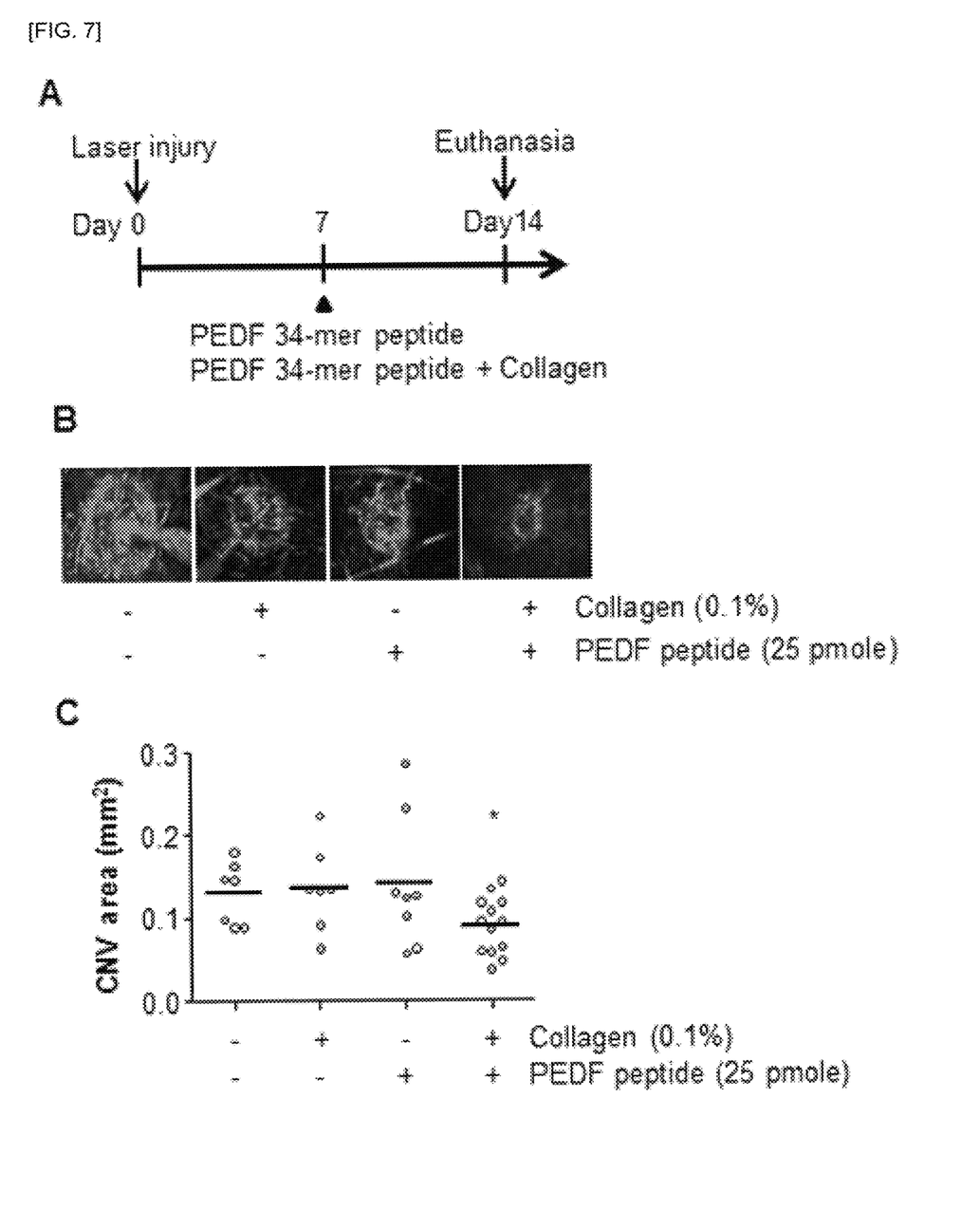
FIG. 7 shows the antiangiogenic effect by treating the mixture of the 34-mer pigment epithelium derived factor peptide and the collagen type I after the neovascularization was completely formed at 7 days after the laser irradiation.

<Example 6> Confirmation of Effect of Combined Treatment of Collagen Type I and 34-Mer Pigment Epithelium Derived Factor Peptides in Animal Models with Complete Neovascularization To confirm the effect for treating the neovascularization in a fully neovascularized animal model, PBS alone was administered to the control group on day 7 after the neovascularization completely occurred after laser irradiation in a choroidal neovascularization animal model fabricated as shown in FIG. 7A, and the experimental groups were administered with 0.1% collagen type I alone, 25 pmol 34-mer pigment epithelium derived factor peptide alone, and 0.1% collagen type I and 25 pmol 34-mer pigment epithelium derived factor peptide mixtures, respectively, once.

As a result, as shown in FIG. 7B and FIG. 7C, each alone treatment group showed almost no angiogenesis inhibitory effect similar to that of the control group, but the angiogenesis inhibitory effect was confirmed in the mixture treatment group.

Since it is confirmed that the neovascularization already created also can be effectively treated by the mixture of the collagen type I and the 34-mer pigment epithelium derived factor peptide, from the above results, it is possible to apply as an agent for the treatment of neovascular disease already advanced.

<Example 7> Confirmation of Mechanism of Action of Combined Treatment Effect of Collagen Type I and 34-Mer Pigment Epithelium Derived Factor Peptide HUVECs cells were treated with recombinant human VEGF-165 to activate the VEGF signaling mechanism, followed by administration of 0.2 or 1 pmol/ml 34-mer pigment epithelium derived factor peptide alone and mixture of 0.05% collagen type I and 1 pmol/ml 34-mer pigment epithelium derived factor peptide, and western blots were performed to confirm signaling mechanisms.

In addition, the tube formation of HUVECs cells induced by VEGF was confirmed to be dependent on the mechanism of action using an inhibitor of the identified mechanism of action.

Figure 8:
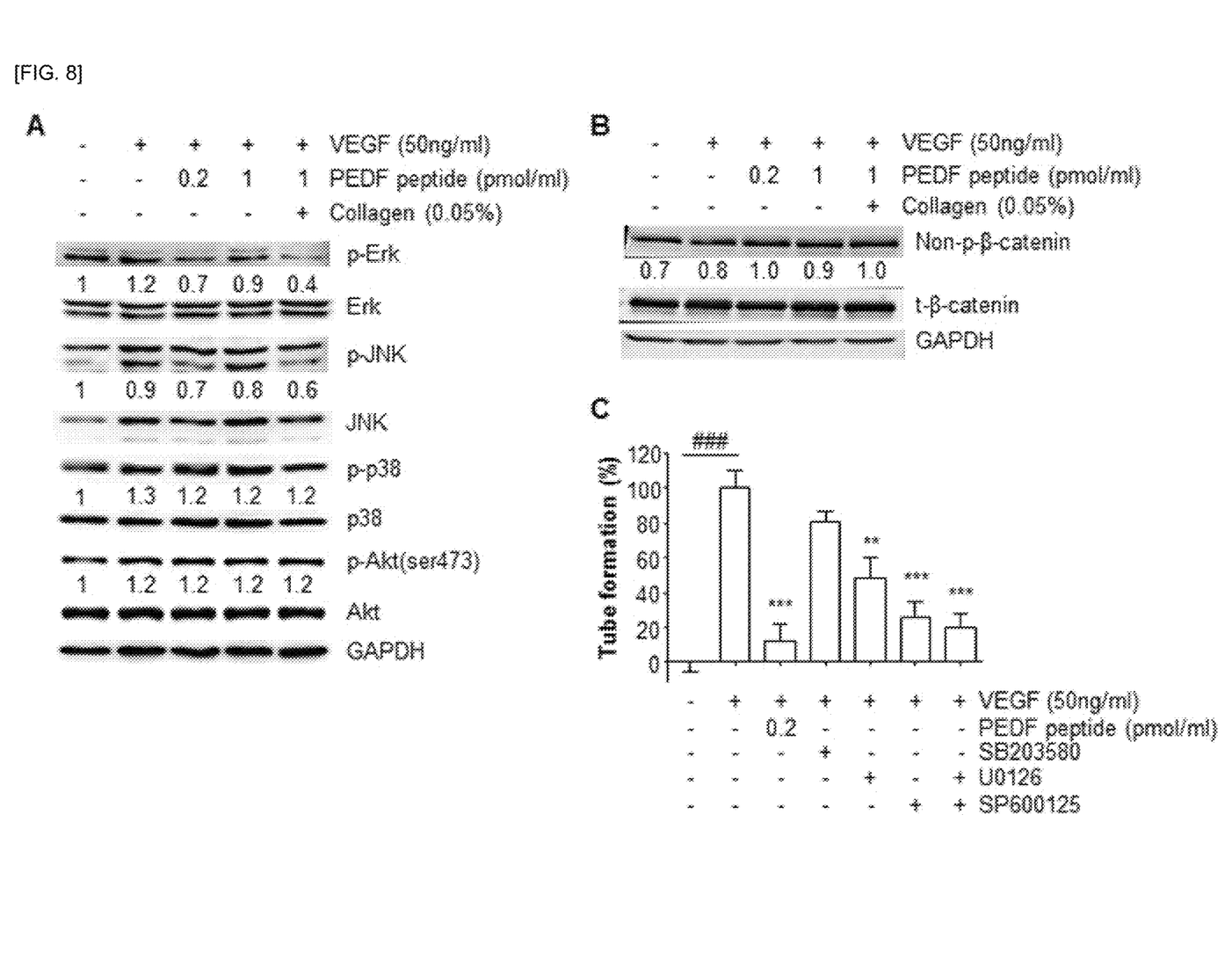
FIG. 8 shows the results of confirming the mechanism of action of the mixture of the 34-mer pigment epithelium derived factor peptide and collagen type I in HUVECs cells.

As a result, mixture of the collagen type I and the 34-mer pigment epithelium derived factor peptide inhibited the activation of JNK and ERK signaling mechanism among MAPK signaling mechanism such as JNK, p38, and ERK and Akt signaling mechanism included in the VEGF signaling mechanism, and the pigment epithelium derived factor signaling mechanism such as Wnt/beta-catenin signaling mechanisms, as shown in FIG. 8A and FIG. 8B. As shown in FIG. 8C, the tube formation of HUVECs cells was also reduced by inhibitors of JNK and ERK.

From these results, the mixture of the collagen type I and the 34-mer pigment epithelium derived factor peptide are closely related to JNK and ERK signaling mechanisms, and can be important for the study of antiangiogenic effects of the 34-mer pigment epithelium derived factor peptides.

<Example 8> Confirmation of Permeability of Collagen Type I and 34-Mer Pigment Epithelium Derived Factor Peptide Mixture The light transmittance at visible wavelengths of collagen type I and 34-mer pigment epithelium derived factor peptide mixture was measured at concentrations showing therapeutic effect to analyze the effect of the mixture on the existing visual field upon injection of therapeutic agents.

Collagen type I was dissolved in PBS at concentrations of 0.05, 0.1, and 0.2%, and then mixed with 34-mer pigment epithelium derived factor peptide to measure absorbance in 10 nm units at 380-780 nm visible wavelengths.

Figure 9:
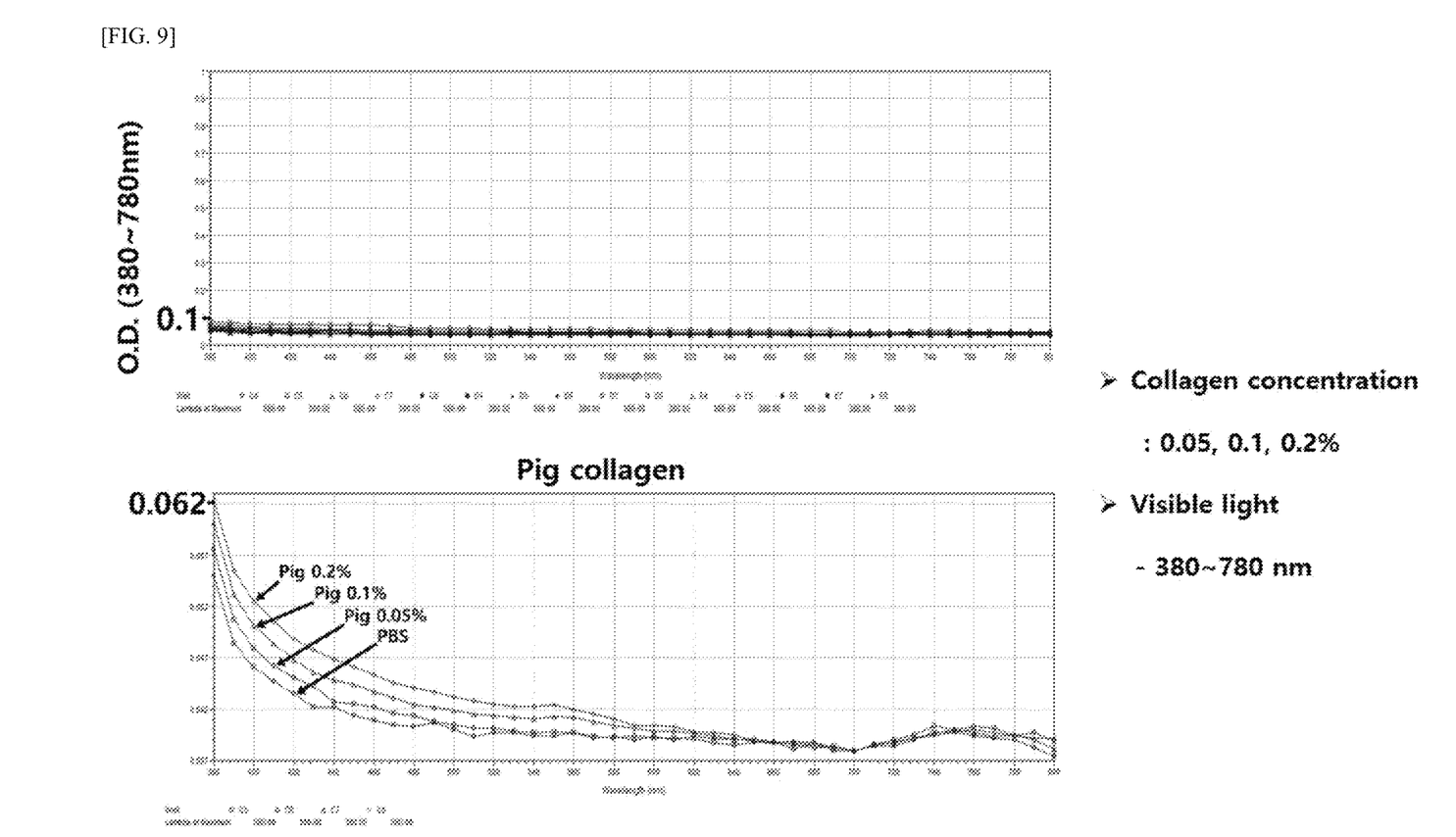
FIG. 9 shows the results of confirming the permeability of the mixture of the collagen type I and the 34-mer pigment epithelium derived factor peptide and the results of confirming the permeability of each mixture by measuring the absorbance in 10 nm unit at 380 to 780 nm visible light wavelength of mixtures of collagen type I dissolved in PBS at concentrations of 0.05, 0.1 and 0.2% and the 34-mer pigment epithelium derived factor peptide, respectively.

As a result, it was confirmed that the wavelength transmission of the visible light of collagen type I and 34-mer pigment epithelium derived factor peptide mixture is similar to that of PBS, as shown in FIG. 9.

Since the injection of collagen type I and 34-mer pigment epithelium derived factor peptide mixture does not interfere with the existing visual field, it can be used as an effective treatment method.

<Example 9> Confirmation of Angiogenic Lesion Treatment Effect of Collagen Type I and 34-Mer Pigment Epithelium Derived Factor Peptide Mixture Mice were anesthetized and laser was irradiated to produce lesions.

Thereafter, 10 µl of the mixture of PEDF 34-mer peptide and collagen type I was dropped into only one eye immediately after the laser irradiation, and was administered once daily for two weeks.

On day 14 after laser irradiation, FITC dextran was injected by retro orbital injection and eyeballs were extracted to perform a flat mount and the treatment of the lesion was confirmed.

Figure 10:
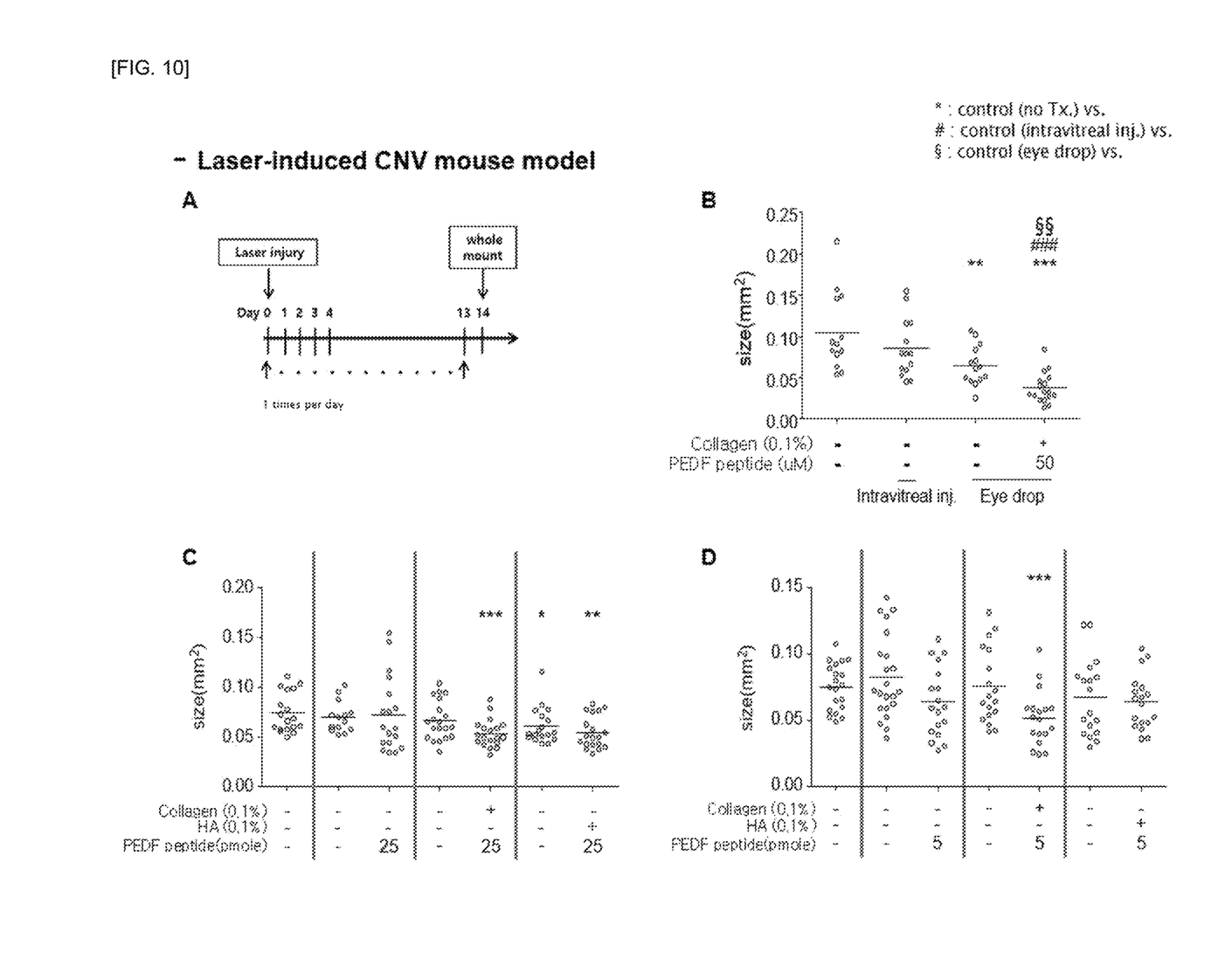
FIG. 10 shows the result of confirming the therapeutic effect on the angiogenic lesion of eye drop of the collagen type I and the 34-mer pigment epithelium derived factor peptide mixture.

As a result, as shown in FIG. 10B, the mixture of PEDF 34-mer peptide and collagen showed a therapeutic effect at the concentrations of 50, 25, and 5 pmole and at 50 pmole concentration, the treatment effect was also observed in the eyeball opposite to the one administered.

In addition, as results of comparing the therapeutic effect of the mixture of 5 and 25 pmole of PEDF 34-mer peptide with collagen or HA as shown in FIG. 100 and FIG. 10D, at 25 pmole, the two mixtures showed efficacy, but at lower concentrations of 5 pmole, only the mixture with collagen showed a therapeutic effect.

<Example 10> Stability Confirmation

In order to confirm the stability of the mixture of PEDF 34-mer peptide and collagen, the mixture of PEDF 34-mer peptide and collagen and the PEDF 34-mer peptide were stored for 6 weeks at 4° C. and room temperature (RT), and stability of PEDF 34-mer peptide and PEDF 34-mer peptide and collagen mixture, which were prepared immediately before the experiment, were compared.

Tube formation assay for each mixture was performed to confirm angiogenesis inhibitory ability.

Figure 11:
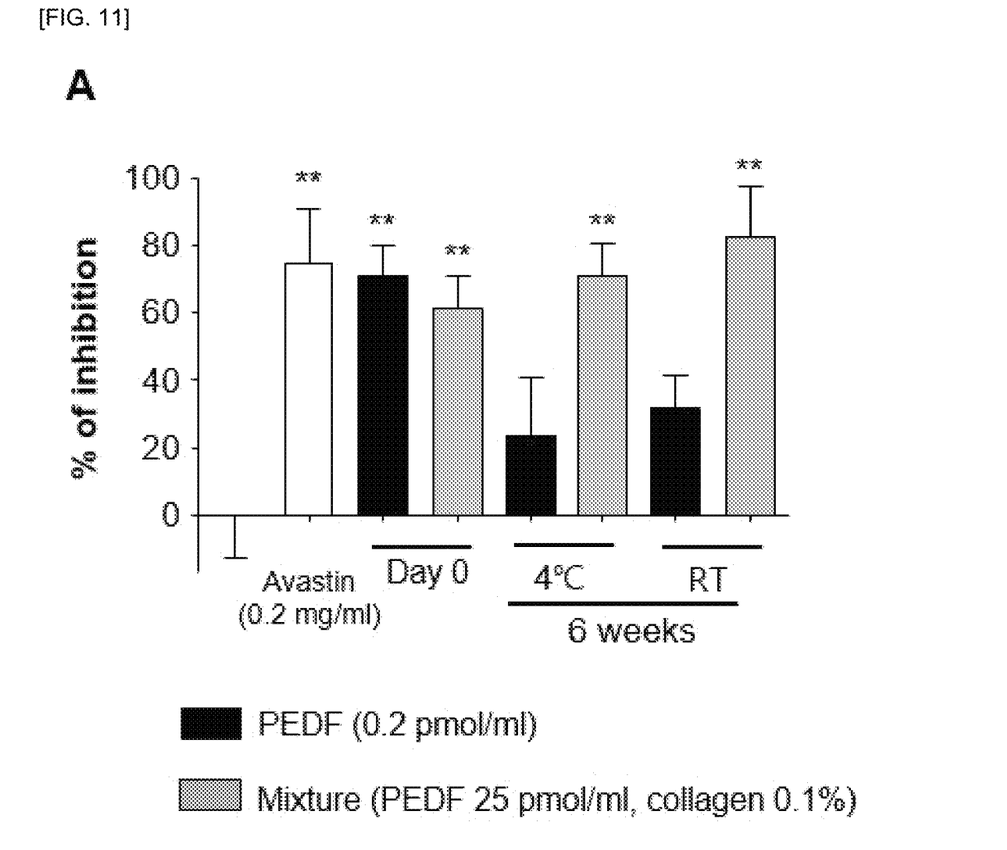
FIG. 11 shows HUVECs tube formation analysis confirming the stability of the mixture of the collagen type I and the 34-mer pigment epithelium derived factor peptide.

As a result, as shown in FIG. 11, the experimental group treated with the PEDF 34-mer peptide alone stored for 6 weeks did not inhibit the tube formation compared with the experimental group treated with the PEDF 34-mer peptide prepared immediately before the experiment, but it was confirmed that the tube formation ability of the mixture of collagen and PEDF 34-mer peptide was not reduced compared to the mixture prepared immediately before the experiment.

From the above results, it was confirmed that stability was maintained when the PEDF 34-mer peptide formed a mixture with collagen.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A method of treating an ocular neovascular disease in a subject in need thereof, comprising:
   administering to the subject a pharmaceutical composition comprising a collagen type I and a 34-mer pigment epithelium derived factor (PEDF) peptide consisting of SEQ ID NO: 1, as an active ingredient, wherein the 34-mer PEDF peptide has a concentration of 0.2-50 pmol/ml and the collagen type I maintains an intraocular antiangiogenic effect of the PEDF peptide,
   wherein the ocular neovascular disease is treated.

2. The method of claim 1, wherein the collagen type I is isolated from pigs.

3. The method of claim 1, wherein the ocular neovascular disease is selected from the group consisting of corneal neovascular disease, diabetic retinopathy, choroidal neovascular disease and age-related macular degeneration.

4. The method of claim 1, wherein the pharmaceutical composition comprises 0.01-50% weight of the 34-mer PEDF peptide and 50-99.99% weight of the collagen type I.

5. The method of claim 1, wherein the pharmaceutical composition is a form of eye drops, a gel ophthalmic ointment or an injection.

6. The method of claim 1, wherein the pharmaceutical composition further comprises a pharmaceutically acceptable carrier.

* * * * *

SEQUENCE LISTING

<160> NUMBER OF SEQ ID NOS: 1

<210> SEQ ID NO 1

```
-continued

<211> LENGTH: 34
<212> TYPE: PRT
<213> ORGANISM: Artificial Sequence
<220> FEATURE:
<223> OTHER INFORMATION: pigemented epithelium derived factor peptide

<400> SEQUENCE: 1

Asp Pro Phe Phe Lys Val Pro Val Asn Lys Leu Ala Ala Ala Val Ser
1               5                   10                  15

Asn Phe Gly Tyr Asp Leu Tyr Arg Val Arg Ser Ser Thr Ser Pro Thr
            20                  25                  30

Thr Asn
```